US005972878A

United States Patent [19]

Sonnenberg et al.

[11] Patent Number: 5,972,878

[45] Date of Patent: Oct. 26, 1999

[54] USE OF SUBSTITUTED 2-ACETYLBENZOFURANS AS ODORIFEROUS SUBSTANCES

[75] Inventors: Steffen Sonnenberg; Peter Wörner; Ulrich Harder, all of Holzminden, Germany

[73] Assignee: Haarmann & Reimer GmbH, Holzminden, Germany

[21] Appl. No.: 08/919,658

[22] Filed: Aug. 28, 1997

[30] Foreign Application Priority Data

Sep. 3, 1996 [DE] Germany ........................... 196 35 655

[51] Int. Cl.$^{6}$ .............................. A61K 7/46; C11B 9/00; C07D 307/79

[52] U.S. Cl. .............................. 512/13

[58] Field of Search .............................. 512/13

[56] References Cited

U.S. PATENT DOCUMENTS

| | | | |
|---|---|---|---|
| 3,513,239 | 5/1970 | Willey et al. . | |
| 3,917,871 | 11/1975 | Winter et al. . | |
| 4,006,234 | 2/1977 | Child et al. . | |
| 5,250,441 | 10/1993 | Vogt et al. | 436/111 |

FOREIGN PATENT DOCUMENTS

| | | |
|---|---|---|
| 553621 | 6/1957 | Belgium . |
| 1377324 | 12/1974 | France . |
| 2307535 | 8/1973 | Germany . |

OTHER PUBLICATIONS

R.B. Gammill, et al., Oxymetalation of Khellin. Solvomercuration, Osmylation, and Palladium–Catalyzed Oxidation of the Furan Ring in Khellin. The Synthesis of Highly Oxygenated Chromones and 2–Substituted Furochromones, J. Org. Chem., vol. 51, No. 16, pp. 3116–3123, (1986).

M. Gill, An Efficient Friedel–Crafts Synthesis of 2–Acylbenzofurans, Tetrahedron, vol. 40, No. 3, pp. 621–626, (1984).

Valades et al. ". . . Synthesis of benzofurans and derivatives", CAPIUS Abstract No. 1976: 179, 948, 1976.

Casimir et al., "Fluorometric Determination of Methyl Anthranilate in Concord Grape Juice" Journal of the AOAC, vol. 59, No. 2 (1976) pp. 269–272.

Ekanayake et al., "Improved Diazotization–coupling Technique for Analysis of Methyl Anthranilate in Grape Products", Journal of Food Science, vol. 55, No. 3 (1990) pp. 877–878.

Rink et al., "Conversion of $N^{G}$–Urethane Protected Arginine to Ornithine in Peptide Solid Phase Synthesis" Tetrahedron Letters, vol. 25, No. 6, (1984) pp. 621–624.

Grieco, et al. Fluoroprostaglandins: Total Synthesis of (+)–13–Fluoroprostanglandin $F_{2\alpha}$Methyl Ester J. Org. Chem., vol. 50, (1985) pp. 3111–3115.

Nielek et al., "Synthesis and Properties of 2,3,5,6–Tetrahydro–6–(3–methyl–benzofuran–2–yl)imidazo [2,1–b]thiazole", vol. 115, (1982) pp. 1247–1251.

Adamson, "The Value of Perfume Raw Materials in Soap" Perfumer & Flavorist, vol. 9, (Apr./May 1984) pp. 55–64.

Haarmann & Reimer, Fragrance Division—Corporate Rule H & R Perfumery No. 13 (Nov. 18, 1994) 8 pages.

*Primary Examiner*—Jeffrey C. Mullis
*Attorney, Agent, or Firm*—Sprung Kramer Schaefer & Briscoe

[57] ABSTRACT

Certain 2-carbonylbenzofurans and 2-carbonyl-2,3-dihydrobenzofurans are excellent odoriferous substances.

9 Claims, No Drawings

USE OF SUBSTITUTED 2-ACETYLBENZOFURANS AS ODORIFEROUS SUBSTANCES

The invention relates to substituted 2-carbonylbenzofurans and substituted 2-carbonyl-2,3-dihydrobenzofurans as odoriferous substances.

As a result of the generally inadequate availability of naturally occurring odoriferous substance components, the constantly increasing and changing perfumistic requirements and the loss of customary odoriferous substances because of toxicological, ecological and economic unacceptability, there is still a need for compounds having valuable odoriferous substance properties.

The invention relates to the use of compounds of the formula (I)

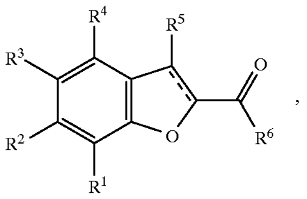

, wherein the broken line denotes a bond which may or may not be present and $R^1$ to $R^4$ independently of one another denote hydrogen, $C_1$–$C_3$-alkyl or $C_1$–$C_3$-alkoxy and $R^5$ and $R^6$ independently of one another denote hydrogen, $C_1$–$C_4$-alkyl or $C_2$–$C_4$-alkenyl, as odoriferous substances.

Numerous 2-carbonylbenzofurans have been mentioned, inter alia, for their use as intermediate products in the preparation of pharmaceutical products (for example U.S. Pat. No. 4,006,234; German Offenlegungsschrift 2 307 535; U.S. Pat. No. 3,513,239, Abstract: M. Gill Tetrahedron 40 (1984), 621). Use as a flavouring substance in instant coffee has indeed been described for 2-formylbenzofuran and 2-acetylbenzofuran, but the value of these compounds as odoriferous substances with numerous facets in terms of odour and their properties in compositions have not been recognized.

The compounds (I) either are known or can be prepared analogously to known processes. Thus, for example, the 2-carbonylbenzofurans (IV) can be prepared in accordance with the following equation:

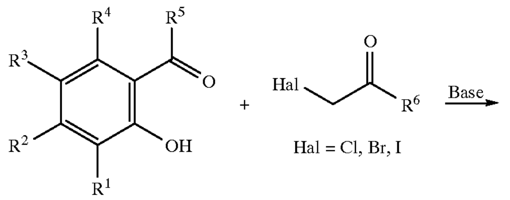

(II) (III)

-continued

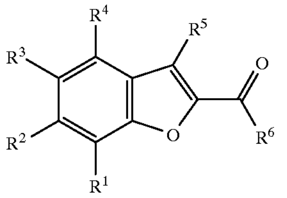

(IV)

Reaction of hydroxypropiophenone (II) with chloroacetone (III) using potassium hydroxide in ethanol gives, by Stroemer-Schaefer condensation, 2-acetyl-3-ethylbenzofuran (IVj, $R^1$–$R^4$=H, $R^5$=$C_2H_5$, $R^6$=$CH_3$) in a yield of about 80% (Belgian Patent Specification 553 621; (Chem. Abs. 5, 22016)).

According to Chem. Ber. 115 (1982), 1247, with hydroxyacetophenone (II) and potassium carbonate, as the base, 2-acetyl-3-methylbenzofuran (IVg, $R^1$–$R^4$=H, $R^5$–$R^6$=$CH_3$) results correspondingly in a yield of about 28%.

Similar 2-carbonylbenzofurans are obtained in yields of about 53% by the additional use of crown ethers as phase transfer catalysts (R. B. Gammill and S. A. Nash, J. Org. Chem. 51 (1985), 3116).

Another method for preparation of the 2-carbonylbenzofurans (IV) is gentle acylation of 2-(trimethylsilyl)benzofuran compounds starting from the corresponding benzofuran derivatives by the process of M. Gill in Tetrahedron 40 (1984), 621.

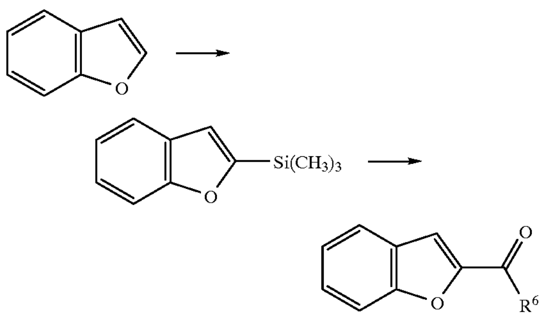

The 2-carbonyl-2,3-dihydrobenzofurans of the formula (V)

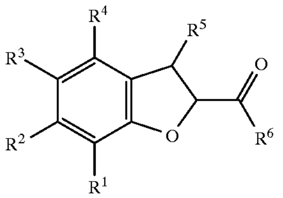

can be prepared by reduction from the above-mentioned 2-carbonylbenzofurans (IV), for example by hydrogenation in ethanol by means of hydrogen in the presence of a Pd catalyst and subsequent oxidation with pyridinium chlorochromate in methylene chloride.

The compounds (I) to be used according to the invention have interesting odoriferous substance properties:

In addition to a generally flowering note, they have a large number of facets in terms of odour. Some of the properties in terms of odour are described in the following:

In the case of 2-formylbenzofuran, in addition to the tonka- and almond-like note, there is also a very cinnamony and anthranilate-like note, which produces a significant radiance in compositions.

In the case of 2-acetylbenzofuran, in addition to the usual almond-like and flowering odour, there is also a fine anthranilate-like and coumarin-like note, which has the effect of an outstanding harmonization in compositions due to its fullness and softness.

2-Acetylbenzofuran can furthermore have the effect of a nitro-musk note as a nuance in combination with various musk odoriferous substances.

The 2-carbonyl-2,3-dihydrobenzofurans are in general similar to the 2-carbonylbenzofurans used as regards their properties in terms of odour. However, the 2-carbonyl-2,3-dihydrobenzofurans have further notes: thus, for example, a green, melon-like and light flowering odour is additionally present in the case of 2-acetyl-2,3 -dihydrobenzofuran.

2-Acetyl-2,3-dihydro-3-methylbenzofuran has an odour of lilies of the valley and has a high diffusion, which produces a great impact in compositions.

It has furthermore been found that the compounds (I) have a very high productiveness and diffusion, which produce a significant effect in a composition even in small amounts.

The compounds (I) are distinguished by a high stability to the most diverse acid, neutral and alkaline media. Thus, for example, a solution of the compounds (I) in toluene, in hydrochloric acid or in sodium hydroxide solution can be stirred to the greatest extent without damage, even at higher temperatures.

Because of the comparatively good stability of the compounds (I), other known odoriferous substances with the same odour but with a low stability can be replaced.

Thus, for example, 2-acetyl-3-methylbenzofuran is a substitute which is more stable in terms of odour and colour for the odoriferous substance methyl anthranilate because of the potent anthranilate-like odour.

The overviews given in the examples in Tables 1 and 2 show some of the olfactory properties of the 2-carbonylbenzofurans and 2-carbonyl-2,3-dihydrobenzofurans to be used according to the invention.

The compounds (I) to be used according to the invention can be easily combined with other odoriferous substances in various different ratios of amounts to give novel, interesting odoriferous substance compositions, the amount being 0.01 to 50% by weight, preferably 0.01 to 10% by weight, based on the entire composition.

As well as in fine perfumery, such compositions can be used for perfuming cosmetics, such as creams, lotions, aerosols, toilet soaps, domestic products, such as cleaning compositions and detergents, softeners, disinfectants and textile treatment compositions, the amount of the odoriferous substance compositions being 0.1 to 40% by weight, preferably 0.5 to 20% by weight, based on the entire product.

The percentage data of the following examples are in each case based on the weight.

EXAMPLES

Example 1

A mixture of 250 g (1.66 mol) of 2-hydroxy-4-methylacetophenone, 460 g (3.3 mol) of potassium carbonate and 44 g (0.16 mol) of crown ether 18-C-6 in 1,200 ml of toluene and 1,200 ml of water was heated under reflux for three hours with the continuous addition of 170 g (1.8 mol) of chloroacetone. The mixture was then allowed to cool to room temperature, the phases were separated and the organic phase was washed twice with 200 ml of sodium hydroxide solution each time and with 200 ml of water. The toluene was then distilled off under reduced pressure and the resulting residue was distilled in vacuo in a thin film evaporator. Finally, the distillate was recrystallized from ethanol.

131 g of 2-acetyl-3,5-dimethylbenzofuran (boiling point 92–96° C./0.2 mbar, melting point 66.3–66.5° C.) were obtained.

Example 2

2-Trimethylsilylbenzofuran from benzofuran: 680 ml (1.1 mol of n-butyllithium (1.6 molar) were added dropwise at −75° C. to a solution of 100 g (0.85 mol) of benzofuran in 1,100 ml of tetrahydrofuran and the mixture was subsequently stirred for a further two hours. 138 g (1.3 mol) of precooled trimethylchlorosilane in 200 ml of tetrahydrofuran were then added, and the mixture was stirred at −75° C. for two hours and allowed to warm to room temperature in the course of a further 16 hours. It was then diluted with 2,000 ml of hexane and after filtration, the solvent was distilled off in vacuo.

168 g of 2-Trimethylsilylbenzofuran were obtained with a purity of >95% and was further reacted directly.

Acylation of 2-trimethylsilylbenzofuran to give 2-isobutyrylbenzofuran: 52.4 g (0.28 mol) of titanium tetrachloride were added to a solution of 40 g (0.21 mol) of 2-trimethylsilylbenzofuran and 25 g (0.23 mol) of isobutyryl chloride in 250 ml of methylene chloride at −78° C. After 15 minutes, the reaction was interrupted by the addition of 800 ml of water, and the mixture was warmed to room temperature. The reaction mixture was then diluted with 100 ml of water and extracted three times with 300 ml of ether each time. After drying, filtration and removal of the solvent in vacuo, the residue was distilled. For further purification, the distillate was subjected to column chromatography or recrystallized from ethanol.

30 g of 2-isobutyrylbenzofuran (boiling point 89 to 92° C./1 mbar) were obtained.

TABLE 1

2-Carbonylbenzofuran

| Compound IV | $R^1$ | $R^2$ | $R^3$ | $R^4$ | $R^5$ | $R^6$ | Boiling point [° C./mbar] Melting point [° C.] | Odour description |
|---|---|---|---|---|---|---|---|---|
| a | H | H | H | H | H | H | 94–98/4<br>— | Anthranilate-like, sweet, tonka almond, cinnamony |
| b | H | H | H | H | H | $CH_3$ | 98–103/2<br>72, 4–73, 1 | Anthranilate-like, orange blossom, jasmine, tonka, |

TABLE 1-continued

2-Carbonylbenzofuran

| Compound IV | $R^1$ | $R^2$ | $R^3$ | $R^4$ | $R^5$ | $R^6$ | Boiling point [° C./mbar] Melting point [° C.] | Odour description |
|---|---|---|---|---|---|---|---|---|
| | | | | | | | | ylang, sweet |
| c | H | H | H | H | H | $C_2H_5$ | 89–93/2, 5<br>49, 4–50, 0 | Flowery, jasmine, anthranilate-like, mushroomy, aniseed |
| d | H | H | H | H | H | $C(CH_3)_3$ | 96–98/1, 3<br>— | Sweet, almond, honey, aniseed, woody, warm |
| e | $OCH_3$ | H | H | H | H | $CH_3$ | 121–126/2<br>93, 7–93, 8 | Anthranilate-like, coumarin, sweet, leathery, honey |
| f | H | H | H | H | H | $CH{=}CH{-}CH_3$ | 113–121/1<br>57, 5–58, 4 | Coumarin, lactone, fruity flowery |
| g | H | H | H | H | $CH_3$ | $CH_3$ | 82–86/0, 2<br>37, 2–38, 3 | Anthranilate-like, blossom, sweet tonka, jasmine |
| h | H | H | $CH_3$ | H | $CH_3$ | $CH_3$ | 92–96/0, 2<br>66, 2–66, 5 | Orange blossom, sweet, tonka, anthranilate-like |
| i | H | H | H | H | $CH_3$ | $C_2H_5$ | 93–96/0, 2<br>87, 8–87, 9 | Sweet, flowery, anthranilate-like, tonka |
| j | H | H | H | H | $C_2H_5$ | $CH_3$ | 88–90/1<br>35, 5–35, 7 | Heliotrope, sweet, ylang, erogenous, musk, blossom |
| k | H | H | H | H | H | $C_3H_7$ | 111–116/1<br>63, 3–63, 8 | Flowery, fruity, almond, sweet, aniseed |
| l | H | H | H | H | H | $CH(CH_3)_2$ | 89–92/1<br>— | Fruity, nut, coumarin, sweet |

Example 3

10 g (0.06 mol) of 2-acetyl-3-methylbenzofuran are dissolved in 200 ml of ethanol and hydrogenated under 20 bar at 50° C. with the addition of 5% of Pd/C (5% strength), until the uptake of hydrogen has ended. After the catalyst has been filtered off, the ethanol is removed in vacuo.

The residue is then dissolved in 20 ml of methylene chloride and the solution is added to a stirred suspension of 29.2 g (0.14 mol) of pyridinium chlorochromate in 100 ml of methylene chloride at 25° C. After one hour, the reaction is interrupted by addition of 500 ml of ether and the reaction mixture is filtered. The filtrate is freed from the solvent in vacuo and the residue is distilled in vacuo. For further purification, the product is subjected to column chromatography.

4.1 g of 2-acetyl-2,3-dihydro-3-methylbenzofuran (boiling point 70 to 74° C./0.23 mbar) were obtained.

TABLE 2

2-Carbonyl-2,3-dihydrobenzofuran

| Compound V | $R^1$ | $R^2$ | $R^3$ | $R^4$ | $R^5$ | $R^6$ | Boiling point [° C./mbar] | Odour description |
|---|---|---|---|---|---|---|---|---|
| a | H | H | H | H | H | $CH_3$ | 70–74/0, 23 | Fresh, flowery, melon, green, orange blossom |
| b | H | H | H | H | $CH_3$ | $CH_3$ | 80–90/0, 2 | Fresh, flowery, lilies of the valley, anthranilat-like |

The following compositions, use examples 1 to 4, are preferably suitable for fine perfuming of cosmetics, such as creams, lotions, aerosols and toilet soaps.

USE EXAMPLES

The intended use and the perfumistic actions of the compounds are demonstrated by some examples in the following.

Use Example 1

| Name | Parts by weight |
|---|---|
| Linalyl acetate | 70 |
| Lemon oil | 50 |
| Lemon Oil Formosa/Java | 3 |

-continued

| Name | Parts by weight |
|---|---|
| Lavandin oil 30/32% Abrialis | 70 |
| Hydroxycitronellal | 30 |
| Geranium Identoil (Afrik. type) | 50 |
| Geraniol 70 | 30 |
| Benzyl acetate | 15 |
| α-Hexylcinamaldehyde | 15 |
| Ylang Ylang oil II | 10 |
| Benzyl salicylate | 100 |
| Isoamyl salicylate | 100 |
| Anethol | 2 |
| Anisyl alcohol | 35 |
| Anisaldehyde | 25 |
| Ethyl vanillin (10% in DEP) | 5 |
| Coumarin | 30 |
| Vetiver oil Bourbon | 10 |
| Patchouli oil | 25 |
| Sandal H & R | 40 |
| Mousse C Abs. Verit. (50% in TEC) | 15 |
| Tonalide | 20 |
| Galaxolide (50% in DEP) | 40 |
| Dipropylene glycol | 190 |
| 2-Propionyl-3-methylbenzofuran | 20 |
| Total | 1000 |

The use of 2-propionyl-3-methylbenzofuran produces marked balsamic facets in this male fougere note. The impact in this brute type is furthermore increased significantly.

DEP=diethylphthalate

TEC=triethyl citrate

Use Example 2

| Name | Parts by weight |
|---|---|
| Styrolyl acetate | 4 |
| Dihydromyrcenol | 4 |
| Lemon oil | 20 |
| γ-Undecalactone | 2 |
| Linalool | 10 |
| Phenylethyl alcohol | 8 |
| Citronellol | 6 |
| Benzyl acetate | 15 |
| Hedione | 20 |
| α-Hexylcinamaldehyde | 100 |
| Jasmine base #151 | 25 |
| Ylang base #10372MT | 18 |
| Isoraldein 70 | 50 |
| Eugenol | 4 |
| Isoeugenol | 1 |
| Vanillin | 10 |
| Coumarin | 10 |
| Oryclon | 30 |
| Patchouli oil | 3 |
| Sandal 80 | 50 |
| Galaxolide (50% in DEP) | 20 |
| Bergamot Identoil | 100 |
| Diethyl phthalate | 465 |
| 2-Acetylbenzofuran | 25 |
| Total | 1000 |

In this feminine composition, the use of 2-acetylbenzofuran has the effect of increasing the volume and diffusion and increases the substantivity. Furthermore, a soft orange blossom-like freshness which gives the composition a valuable note is produced.

Use Example 3

| Name | Parts by weight |
|---|---|
| cis-3-Hexenol | 5 |
| Phenylacetaldehyde (50% in DPG) | 90 |
| Hydroxycitronella P | 95 |
| Linalool | 455 |
| Phenylethyl acetate | 10 |
| Phenylethyl alcohol pure | 295 |
| α-Hexylcinamaldehyde | 5 |
| α-Amylcinamaldehyde | 20 |
| β-Ionon | 5 |
| Ethylphenylacetate | 5 |
| 2-Acetyl-3-methylbenzofuran | 15 |
| Total | 1000 |

In this flowery accord, 2-acetyl-3-methylbenzofuran with an orange blossom-like note, significantly increases the radiance and the diffusion. 2-Acetyl-3-methylbenzofuran furthermore helps to increase the tenacity and gives the composition a constant flowery impression in the dry out.

DPG=Dipropylene glycol

Use Example 4

| Name | Parts by weight |
|---|---|
| Phenyl acetaldehyde (50% in DPG) | 20 |
| Lyral | 270 |
| Hydroxycitronellal | 150 |
| Phenylethyl alcohol | 60 |
| Citronellol | 60 |
| α-Hexylcinnamaldehyde | 310 |
| Indole | 120 |
| 2-Acetyl-2,3-dihydrobenzofuran | 10 |
| Total | 1000 |

The use of 2-acetyl-2,3-dihydrobenzofuran adds a fresh nerol-like note to the fragrance pattern and intensifies the natural character of this lily of the valley composition.

We claim:

1. A method for perfuming cosmetic compositions, cleaning compositions, detergent compositions, softener compositions, disinfectant compositions, textile treatment compositions and perfume compositions which comprises adding to said compositions from 0.01 to 10% by weight, based on the total weight of composition, of a compound of the formula (I)

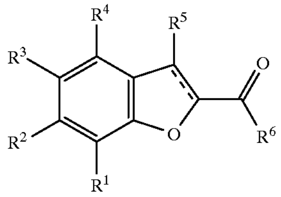

, wherein the broken line denotes a bond which may or may not be present and $R^1$ to $R^4$ independently of one another denote hydrogen, $C_1$–$C_3$-alkyl or $C_1$–$C_3$-alkoxy and $R^5$ and $R^6$ independently of one another denote hydrogen, $C_1$–$C_4$-alkyl or $C_2$–$C_4$-alkenyl.

2. Method according to claim 1, wherein the broken line denotes a bond and $R^1$ to $R^6$ independently of one another represent hydrogen or $C_1$–$C_2$-alkyl.

3. Method according to claim 1, wherein the broken line denotes no bond and $R^1$ to $R^6$ independently of one another represent hydrogen or $C_1$–$C_2$-alkyl.

4. Method according to claim 1, wherein the broken line denotes a bond and $R^1$ to $R^4$ represent hydrogen and $R^5$ and $R^6$ independently of one another represent hydrogen or $C_1$–$C_2$-alkyl.

5. Method according to claim 1, wherein the broken line denotes no bond and $R^1$ to $R^4$ represent hydrogen and $R^5$ and $R^6$ independently of one another represent hydrogen or $C_1$–$C_2$-alkyl.

6. Method according to claim 1, wherein the broken line denotes a bond and $R^1$ to $R^4$ represent hydrogen and $R^5$ and $R^6$ represent $C_1$–$C_2$-alkyl.

7. Method according to claim 1, wherein the broken line denotes a bond and $R^1$ to $R^4$ represent hydrogen and $R^5$ represents $C_1$–$C_2$-alkyl and $R^6$ represents hydrogen or $C_1$–$C_4$-alkyl.

8. A perfume composition comprising from 0.01 to 10% by weight of a compound of the formula (I)

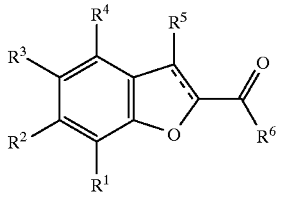

, wherein the broken line denotes a bond which may or may not be present and $R^1$ to $R^4$ independently of one another denote hydrogen, $C_1$–$C_3$-alkyl or $C_1$–$C_3$-alkoxy and $R^5$ and $R^6$ independently of one another denote hydrogen, $C_1$–$C_4$-alkyl or $C_2$–$C_4$-alkenyl.

9. The composition of claim 8, wherein said composition is a perfume oil.

* * * * *